(12) United States Patent
Wheeler

(10) Patent No.: US 6,260,360 B1
(45) Date of Patent: Jul. 17, 2001

(54) CONTAINER

(75) Inventor: Arthur Wheeler, Abu Dhabi (AE)

(73) Assignee: Isosafe Limited, Hampshire (GB)

(*) Notice: Subject to any disclaimer, the term of this patent is extended or adjusted under 35 U.S.C. 154(b) by 0 days.

(21) Appl. No.: 09/555,055

(22) PCT Filed: Nov. 24, 1998

(86) PCT No.: PCT/GB98/03513

§ 371 Date: Jul. 19, 2000

§ 102(e) Date: Jul. 19, 2000

(87) PCT Pub. No.: WO99/27312

PCT Pub. Date: Jun. 3, 1999

(30) Foreign Application Priority Data

Nov. 24, 1997 (GB) .................................... 9724795

(51) Int. Cl.[7] .................................................. F25B 21/02
(52) U.S. Cl. ............................ 62/3.6; 362/3.7; 362/371; 362/405
(58) Field of Search .............................. 62/3.6, 3.62, 3.7, 62/259.2, 371, 405

(56) References Cited

U.S. PATENT DOCUMENTS

| | | |
|---|---|---|
| 2,000,882 | 5/1935 | Comstock . |
| 2,942,051 | 6/1960 | Roeder . |
| 2,973,627 | 3/1961 | Lackey et al. . |
| 3,823,567 | 7/1974 | Corini . |
| 4,364,234 | * 12/1982 | Reed .......................................... 62/3 |
| 4,472,945 | 9/1984 | Cech et al. . |
| 4,689,014 | 8/1987 | Krasner . |
| 5,217,064 | 6/1993 | Kellow et al. . |
| 5,363,670 | 11/1994 | Bartilucci . |
| 5,398,510 | * 3/1995 | Gilley et al. ............................. 62/3.6 |
| 5,522,216 | * 6/1996 | Park et al. ............................... 62/3.6 |
| 5,572,873 | 11/1996 | Kellow et al. . |
| 5,603,220 | * 2/1997 | Seaman ................................... 62/3.7 |
| 5,605,047 | 2/1997 | McGrath et al. . |
| 5,661,978 | 9/1997 | Broadfield et al. . |

FOREIGN PATENT DOCUMENTS

| | | |
|---|---|---|
| 35 27 061 | 2/1987 | (DE) . |
| 39 40 649 | 6/1991 | (DE) . |
| 43 19 188 | 12/1994 | (DE) . |
| 0 719 993 | 7/1996 | (EP) . |

* cited by examiner

Primary Examiner—William Doerrler
Assistant Examiner—Melvin Jones
(74) Attorney, Agent, or Firm—Nixon & Vanderhye P.C.

(57) ABSTRACT

A portable container (10) for receiving contents for transport while regulating the temperature of the contents includes a combined heater and/or cooler in the form of a Peltier effect device (50), a removable inner receptacle (70) for receiving the contents, an air gap around the outside of the inner receptacle, and a control unit (62) for controlling the Peltier effect device so as to regulate the temperature of the air around the outside of the inner receptacle and thereby regulate the temperature of the contents of the inner receptacle. The control unit can have a temperature logging system for recording the temperature history of the contents of the container.

28 Claims, 4 Drawing Sheets

CONTAINER

The present invention relates to a container.

The increasing incidence of organ transplants, and the increasing use of temperature-sensitive drugs in the treatment of disease in both humans and animals, has led to a need for a reliable portable container for such organs and drugs. It is currently usual for organs and drugs to be transported in boxes packed in ice. This is unsatisfactory for a number of reasons.

Firstly, the use of ice means that the highest temperature which the organs or drugs can be kept at is freezing point, or 0° C. Ice crystals will start forming at this temperature, and the growth of these ice crystals can damage the cells of an organ being transported for transplant, unless steps are taken to avoid this. In addition, 0° C. may not be the optimum temperature at which drugs should be kept.

Secondly, the ice will melt in time, and so the temperature at which the drugs or organs will be held is not steady. It may be necessary to replenish the ice during transportation.

To avoid these problems, it is desirable to provide a container with some means of regulating its temperature, for example with a Peltier effect device which can heat or cool the contents and a control unit.

A further use of medical containers is in the transport of samples of infectious or contaminated material. For example, samples of such material may need to be taken to a laboratory for analysis. It is frequently necessary to maintain such samples at given temperatures, to ensure that bacteria in the samples are still alive when they reach the laboratory and can then be cultured and identified. However, it will be appreciated that transport of such samples poses a number of problems. In particular, following such transportation, it is necessary to ensure that the container is properly sterilized afterwards, to prevent cross-contamination. This can be done by washing or autoclaving, but it will be understood that these methods may not be ideally suited to cleaning a Peltier device.

According to a first aspect of the invention, there is provided a portable container for receiving contents for transport whilst regulating the temperature of the contents, the portable container comprising heating and/or cooling means in the form of a Peltier effect device, a removable inner receptacle for receiving the contents, an air gap around the outside of the inner receptacle, and a control unit for controlling the Peltier effect device so as to regulate the temperature of the air around the outside of the inner receptacle and thereby regulate the temperature of the contents of the inner receptacle.

The heating and/or cooling means may comprise a heating means only, or a cooling means only. However, it is preferred that both heating and cooling means are provided.

The control of the temperature of the air in the air gap around the inner receptacle enables regulation of the temperature of the contents whilst still permitting the inner receptacle to be removed. Removal of the inner receptacle is useful, for example enabling it to be washed or autoclaved. In addition, when removed the inner receptacle may be placed in a refrigerator. It may thus be refrigerated to the desired temperature, before being placed into the main container, which can then be closed and activated to regulate the temperature of the contents of the inner receptacle. This reduces the amount of power used by the portable container, as it is only necessary to keep the contents cold, rather than having to cool them down initially. If for example the container is powered by a battery, then the length of time for which the container can keep its contents cold, and thus the length of journey which can be undertaken, can be increased.

The portable container can be used to carry drugs, tissue samples, organs for transplant, or indeed any other material which must be transported at a given temperature.

The container will generally have an outer housing, with the air gap being defined between the outer housing and the inner receptacle. The outer housing may comprise a base portion and a lid portion.

A fan is preferably provided to assist air circulation in the air gap. This is advantageously provided adjacent to the Peltier device, both for example being located in a lid portion of the container.

Preferably, the container comprises projections which extend from the outer housing of the container to support the inner container. Air can then circulate between the projections around the inner receptacle. In addition, the projections help to locate the inner container securely in the main container.

Preferably, the control unit of the container is arranged to store a desired temperature for the contents of the container, to receive a signal from a temperature sensor located within the container, and to generate a signal to control the Peltier effect device. From a comparison of the sensed temperature signal with the desired temperature, the control unit decides whether to operate the Peltier effect device, and in what sense (heating or cooling the interior of the container). The temperature sensor is preferably arranged to sense the temperature in the air gap. More than one sensor may be provided, e.g. one above the inner receptacle and one below.

The temperature at which the contents of the container are to be maintained can be set permanently in the control unit. However, as the container may be used with different materials, it is preferred that the temperature at which the contents of the container are to be maintained is entered into the control unit.

This information can be entered in any suitable manner. In a preferred version, a keypad is mounted on the container for entering the desired temperature. However, the keypad may be susceptible to damage, and so alternatively or additionally, the container may comprise an electromagnetic or ultrasonic receiver, and the temperature is set using an external transmitter. In a further version, the container may be connectible to a computer, either directly or via a modem, and this is used to set the temperature.

It may be important that the desired temperature, once set, is not changed without authorization, and thus it is preferred that the control unit includes means for verifying the status of a user before the temperature at which the contents of the container are to be maintained is set. If a key-pad is used, then it may be necessary to enter a code (such as a PIN) before the set temperature can be changed. Codes can also be used if a radio or a computer system is used to enter the information. A card system, for example using swipe cards, or a system where a key has to be inserted into a lock before the set temperature can be modified, could also be used.

It is also generally desirable to know the temperature history of the contents of the container.

In previous containers, there is no guarantee that the organs or drugs have not been damaged during transit by exposure to inappropriate temperatures, as there is no record of the temperatures to which they have been exposed. Thus, it is preferred that the control unit also comprises a temperature logging system, said temperature logging system providing means to verify the temperature history of the container.

This feature is considered to be of independent inventive merit, and so according to a further aspect of the invention, there is provided a portable container for receiving contents for transport whilst regulating the temperature of the contents, the portable container comprising heating and/or cooling means, and a control unit for controlling the heating and/or cooling means so as to regulate the temperature of the contents of the container, said control unit comprising a temperature logging system, said temperature logging system providing means to verify the temperature history of the contents of the container.

The temperature logging system can take a number of forms. For example, a device similar to a tachograph can be used, to sample the temperature at given intervals and make a mark on a record sheet. The marks could (as in a tachograph) require interpretation in order to be understood. However, in a preferred version, the temperature logging system samples the temperature at intervals, and prints the sampled temperature. It is then only necessary to check the printout to see whether the set temperature has been adhered to. Alternatively, the temperature logging system can be provided with a memory which stores data concerning the temperature history. The information in this memory can be accessed by suitable means such as a computer using a modem, optionally by a remote link, and displayed. As an alternative, the computer can be programmed to check the data itself, and give a simple "safe/unsafe" output. Whatever method is chosen, the temperature history of the contents can be checked when the container arrives at its destination, and the recipient can thus immediately verify whether the contents have been damaged by exposure to inappropriate temperatures during transit. The contents of the container are thus immediately verifiable.

Of course, while it is useful to know that the material being transported has spoiled as a result of being exposed to inappropriate temperatures, it would be better for the material not to spoil at all, to avoid wastage. This is particularly important in the case of organs for transplant. Thus, in a preferred embodiment, the control unit generates an alarm signal if the temperature in the container strays too far from the set temperature. The meaning of "too far" will of course depend on the material being transported, but 3° C. is a typical amount. This alarm signal may take the form of a light on the container or an audible signal, which would alert a person travelling with the container that something is amiss.

Alarm signals can also be generated if the latches holding the container closed are detected as being opened, as this can indicate that the container, and possibly the contents thereof, have been tampered with.

The container can be powered in any suitable manner. However, as the container is intended to be portable, the power for the Peltier device, the control units and the fan motors is preferably derived from a battery, more preferably a rechargeable battery. It is preferred that a back-up power source is also provided, in the form of a second battery, so that even if the main battery is exhausted the container can still regulate the temperature of its contents. An alarm signal can be generated on failure of the main battery, and a further different alarm signal can be generated when the back-up battery falls below a predetermined proportion of its capacity.

Further, it is preferred that the container be sufficiently robust to withstand impacts and shock loading. It is inevitable that accidents will occur, and that containers will be dropped from heights, hit and so on. However, Peltier devices are relatively fragile, and must be protected from severe impacts.

Thus, it is preferred that the Peltier device is mounted in a block of elastomeric material. The provision of this elastomeric element helps to reduce the decelerations undergone by the Peltier device, and thus reduces the shock loads thereon.

This feature is considered to be of independent inventive merit, and so according to a further aspect of the present invention, there is provided a portable container having heating and/or cooling means in the form of a Peltier effect device, wherein the Peltier device is mounted in a block of elastomeric material which is in turn mounted to a housing of the container.

It is further preferred that the Peltier device is connected to an inner heat sink facing the interior of the container and an outer heat sink facing the exterior of the container, the heat sinks being clamped together by clamping means passing through the heat sinks and the elastomeric member. The Peltier device, the heat sinks and the elastomeric member then form a single unit, and the heat sinks and the Peltier device will undergo the same decelerations. It is desirable that the heat sinks remain in intimate thermal contact with the Peltier device, to enable it to function properly, and this feature reduces the risk that they may be jolted apart.

The clamping means can take any suitable form. However, if there is a path of conduction from the inner heat sink to the outer heat sink, then the insulative properties of the container will be compromised, as indeed will the efficiency of the Peltier device. Thus, it is preferred that the clamping means is formed from a plastics material. In a particularly preferred embodiment, the clamping means are nylon bolts.

Of course, if the container is to keep the contents at a given temperature, it is desirable that it have a thermally insulating outer housing, to prevent variations in the external temperature from affecting the temperature of the contents.

A number of ways of constructing thermally insulating containers are known. For example, a Dewar flask has a double-walled construction. The space between the walls is evacuated to provide a vacuum, and the sides of the walls facing the vacuum are silvered. It is also known to use thermally insulating material such as foamed polymer materials such as polyurethane in the walls of containers, to reduce heat conduction across the wall.

It is known to use vacuum panels for thermal insulation. These panels comprise a layer of thermally insulating material enclosed within an evacuated flexible cover, which includes an aluminium layer. When such panels are used to insulate containers, they are normally placed in the hollow walls of the container to reduce the heat passing through the walls by conduction. However, the presence of air in the hollow walls still allows heat transfer through convection.

Preferably, the container comprises an outer housing in the form of an inner wall and an outer wall defining a space therebetween, wherein the space between is the inner and outer walls is at least partially evacuated and is occupied by a solid thermally insulating material.

The inner and outer walls thus define the space which is at least partially evacuated and occupied by the insulating material, in addition to their other function as container walls.

The presence of the thermally insulating material reduces the amount of heat which is transferred through the container walls by means of conduction. Further, heat transfer by means of convection is reduced by the at least partial evacuation of the space between the inner and outer walls. Of course, the greater the degree of evacuation, the less heat is transferred by convection.

This feature is also considered to be of independent inventive merit, and so according to a further aspect of the present invention there is provided a container comprising an inner wall and an outer wall defining a space therebetween, wherein the space between the inner and outer walls is at least partially evacuated and is occupied by a solid thermally insulating material.

Such a container can removably hold contents which are to be thermally insulated from the environment, and will therefore generally have a main body and a closure.

The insulating material can be in the form of a powder. However, it is then necessary for the inner and outer walls to be relatively rigid and strong. Accordingly, it is preferred that the insulating material is rigid. The insulating material will then contribute to the structural integrity of the container as a whole. One suitable insulating material is compacted microporous silica.

If a rigid insulating material is used, it will normally be shaped to occupy the space between the inner and outer walls, for example by being moulded or machined to the required shape.

In a preferred embodiment, the insulating material hinders the passage of infra-red radiation. This can be done by absorbing, reflecting or scattering the infrared radiation, and reduces the amount of heat transferred through the walls of the container by means of radiation.

In a further preferred embodiment, the outer wall is metallized. The metallized layer will attenuate any radiation passing through it, and this also helps to reduce the amount of heat transferred through the walls of the container by means of radiation. Using a metallized outer wall with an insulating material that absorbs infra-red radiation can reduce the amount of heat transferred to very low levels.

Preferably, it is the inner surface of the outer wall that is metallized. This protects the metallized layer from abrasion and so on, which it would be subjected to if it was on the outer surface of the outer wall, and thus prolongs its lifespan.

As an alternative to, or additionally to providing a metallized layer, the outer wall may include a metallic foil layer. The outer wall can be formed as a laminate, incorporating a metallic foil layer.

It is further preferred that the inner wall of the container is metallized. When it is desired to maintain the contents of the container at above ambient temperature, it is important to reduce heat losses from the contents, and metallizing the inner wall reduces the amount of infra-red radiation passing through the inner wall.

Alternatively or additionally, the inner wall may include a metallic foil layer, and may be formed as a laminate incorporating a metallic foil layer.

The metallization or the metallic foil layer of the inner or outer walls can be provided with means for making an electrical connection to provide an electrostatic shield. This can then serve to shield any electrical equipment inside the container from electrical interference. It is envisaged that the insulated container will include an electrical cooling and/or heating means, and the switching of this means could cause interference if it were not shielded.

The space between the inner and outer walls can be at least partially evacuated and then permanently sealed. However, as any material used to form the inner and outer walls will be permeable to some degree, it is preferred that some means of restoring the vacuum be provided. Accordingly, in a further preferred embodiment, there is provided a passageway to allow the space between the inner and outer walls to be communicated with a region outside of the space. The passageway can allow the space between the inner and outer walls to be connected to a pressure gauge, a vacuum pump or the like. The vacuum in the space between the inner and outer walls can then be checked by means of a pressure gauge, and if the vacuum has become overly degraded, as a result of excessive gas permeation through the inner and outer walls, then it can be restored using the vacuum pump.

Of course, means must be provided to ensure that there is no leakage at the passageway. This could be done by providing a plug in the passageway. However, it is preferred that the passageway be provided with a valve, which is normally closed. The valve can then be opened when a pressure gauge, vacuum pump or the like has been connected.

The passageway can be provided at any convenient point on the inner or outer walls, or on e.g. an end wall which connects the inner and outer walls. However, if the passageway is in the outer wall, then there is a risk that an impact or similar could open it, for example by damaging a valve provided on the outer wall. It would be possible to recess a valve in the outer wall to reduce the risk of impact damage. However, it is preferred that the inner wall be provided with the passageway, to substantially eliminate the risk of impact damage to it.

Preferred embodiments of the invention will now be described by way of example only and with reference to the accompanying drawings, in which.

Figure 1:
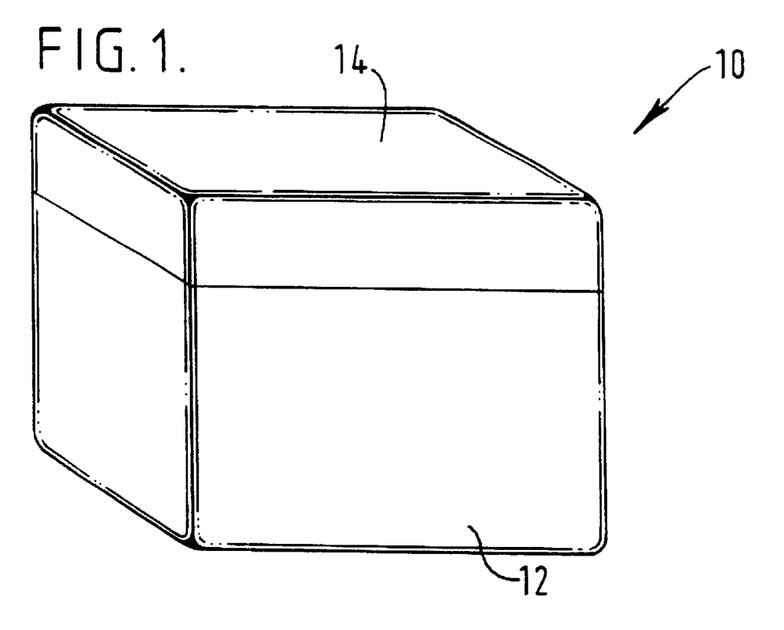
FIG. 1 is a perspective view of a first embodiment of the container in a closed condition.

A container according to a first preferred aspect of the invention is indicated by the reference numeral 10 in FIG. 1. The container comprises a base part 12, in which the contents are accommodated, and a lid 14. The base part and the lid together form an outer housing. The lid 14 is attached to the base 12 by a hinge, clamps or the like, and the container is held closed by latches 76. The container is intended to thermally isolate its contents from the outside, for example to keep the contents cooler than outside.

Figure 2:
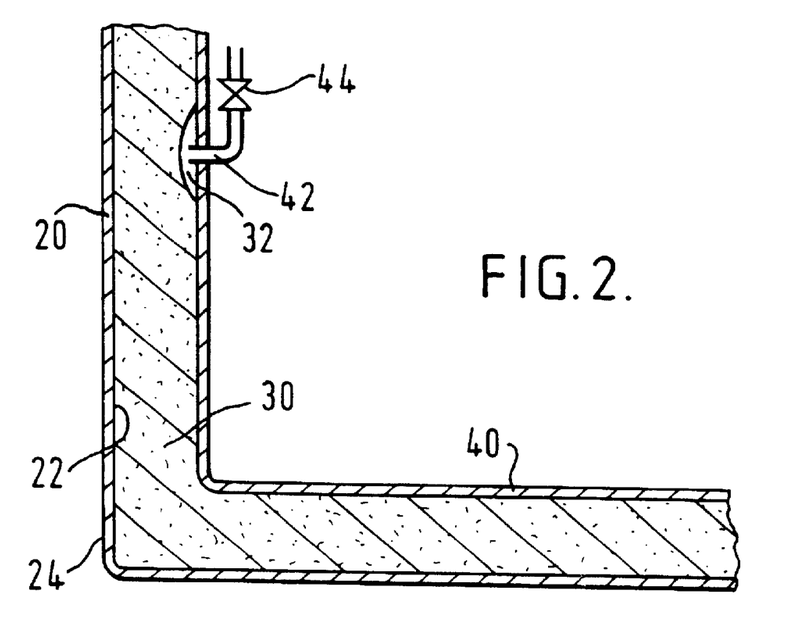
FIG. 2 is a fragmentary schematic cross-sectional view showing the construction of a wall of the first embodiment of the container.

The walls of the container have a sandwich construction, as is best shown in FIG. 2. They comprise an outer wall 20, which forms the external surface of the container, a middle layer 30, and an inner wall 40. The middle layer occupies the space between the inner and outer walls.

The outer wall fulfils a number of functions. It is substantially gas- and liquid-impermeable. It is also important for the material forming the outer wall to be strong, and in particular to be puncture-resistant. In order for the outer wall to meet these various criteria, a resin-bonded laminated material is used. The laminate can include layers of Kevlar (trade mark) or glass- or carbon-fibre reinforced plastics material, to provide the necessary strength. Such materials are very strong in tension, compression and shear, and also display good resistance to shock loads. This is important in helping avoid damage to the container when it is dropped.

The inner surface 22 of the outer wall 20 is metallized. This can be done by spraying, sputtering or vacuum deposition of steel or aluminium. The metallized layer reflects most of the radiation incident thereon, and attenuates the radiation passing through the outer wall 20. If the metallized layer were to be applied to the outer surface 24 of the outer wall 20 rather than the inner surface 22, then it would be subject to scratching, abrasion and the like. Any discontinuities in the metallized layer will allow radiation to pass through it unaffected, and this is clearly undesirable. For this reason, the metallized layer is applied to the inner surface 22 of the outer wall 20.

Alternatively, or additionally, the laminated material can include one or more metallic foil layers. These will not only serve to reflect and attenuate radiation, but also reduce the overall permeability to gases of the outer layer.

One or more of the metallized or metallic foil layers can be provided with means for making an electrical connection to provide an electrostatic shield. This shield will function as a Faraday cage, and will screen any interference which may otherwise be caused by electrical equipment such as heaters, coolers or thermostatic controls inside the container.

The middle layer 30 comprises a porous expanded silica material, which occupies substantially the whole of the lateral width between the inner and outer walls (i.e. the direction transverse to the planes of the walls). The material has a very low thermal conductivity, and serves as a thermal insulator for the container. Such a material is available under the name "Microtherm" from Micropore International Limited of Droitwich, England. In addition to its thermally insulating characteristics, the material is rigid and contributes to the strength and structural integrity of the container.

The expanded silica material can also be treated to further reduce the transmission of infra-red radiation through it. It can incorporate metallic platelets to reflect infra-red radiation, semiconductors such as carbon black or metal oxides to absorb infra-red radiation, and/or high refractive index transmitters to scatter infra-red radiation. These serve to make the middle layer substantially opaque to infra-red radiation. As a result, any infra-red radiation which does pass through the outer wall 20 will not reach the interior of the container 10. Further, the size of the pores in the expanded silica material is less than the mean free path of air molecules.

The inner wall 40 can be constructed in a similar way to the outer wall 20, since it must also be substantially impervious to gases or liquids. However, as the inner wall 40 is less likely to be subjected to direct impacts or similar shocks, it does not require the same strength as the outer wall 20. Further, since any infra-red radiation passing into the container should be prevented from passing through the middle layer 30, there is less need for the inner wall 40 to be metallized in situations where it is desired to maintain the temperature of the contents container below ambient temperature.

Of course, where it is desired to maintain the temperature of the contents of the container above ambient temperature (for example, to prevent freezing of the contents in extremely cold conditions), then it is preferable for the inner wall to be metallized, to prevent heat escaping from the contents through infrared radiation. Additionally, there is less need for the outer wall to be metallized in these conditions. Of course, if the outer wall is not metallized or provided with a metallic foil layer, then the metallized or metallic foil layer of the inner wall can be used to form an electrostatic shield as discussed above.

To allow the container to be used whether the temperature of the contents is to be maintained above or below ambient temperature, both the inner and outer walls can be metallized, to reduce heat transfer by means of radiation either to or from the contents of the container. The less radiation that passes through the inner or outer walls, the less radiation there is to be absorbed, reflected or scattered by the insulating material, and this reduces the conductive heat transport load.

In the manufacture of the container, the inner and outer walls are formed separately. Machined blocks of the expanded silica material are loaded into the floor region and around the sides of the outer wall, and the inner wall is then inserted.

The inner and outer walls 20, 40 are then connected together so that they form a gas- and liquid-impermeable envelope around the middle layer 30. This can be done in a number of ways. For example, welded metallic seals can be used, although this then provides a path of heat conduction into the container. As an alternative, preformed neoprene seals can be bonded to both the inner and outer walls, and this method of sealing substantially reduces heat conduction. In addition, if laminated materials are used to form the inner and outer walls, these can themselves be formed into lips and seals, which can then have an overlaying neoprene layer applied to them to seal them fully. The use of a neoprene layer can also enhance the sealing between the base and the lid of the container when it is closed, as the neoprene layer may be positioned where the base and the lid abut.

To further enhance the insulating properties of the container 10, the envelope is evacuated to a fairly high vacuum, such that the pressure is preferably less than 0.1 mm Hg (0.13 millibars or 13 Pa). The evacuation of the envelope substantially reduces convective heat transfer through the middle layer. It will be appreciated that it is necessary for the inner and outer walls 20, 40 to be impervious to gases in order to create a vacuum inside the envelope. It will also be appreciated that, since any puncture of the envelope will lead to loss of the vacuum, it is important for the outer wall 20 in particular to be strong and puncture-resistant.

Once the vacuum has been established, external atmospheric pressure will tend to push the outer wall inwards. Similarly, atmospheric pressure inside the container will tend to push the inner wall outwards. The tendency for the walls to collapse towards each other is resisted partly by the inherent strength of the walls, and partly by the presence of the insulating material. Because the insulating material helps to resist the compressive forces caused by atmospheric pressure, the walls may be thinner and hence more lightweight than would otherwise be the case.

A passageway 42 is provided in the inner wall 40. This passageway is provided with a valve 44, which is normally closed. The passageway 42 can be connected to a vacuum pump and the valve 44 opened to allow initial evacuation of the space between the walls. In addition, the passageway 42 can be connected to a pressure gauge, allowing the degree of vacuum in the space to be checked. There will inevitably be some leakage through the inner and outer walls 20, 40, and this will tend to degrade the vacuum in the space. If a check shows that the vacuum in the space has become too degraded, the vacuum pump can be reconnected to evacuate the space again and restore the vacuum.

As mentioned above, the expanded silica material is porous, and so the gases in the pores of the material must be removed when the space between the inner and outer walls is evacuated. A small recess 32 in the expanded silica material is shown opposite the passageway 42 in FIG. 2. This provides a greater surface area of the expanded silica material for the vacuum to act upon, and so assists in the degassing of the material. However, the recess can be dispensed with if desired.

As mentioned above, the container 10 comprises a base 12 and a lid 14, to allow access to the contents of the container. The walls of both the base 12 and the lid 14 are formed with a sandwich construction as described above, to provide good thermal insulation. Since the base 12 and the lid 14 are formed as separate parts, the lid 14 is also provided with an opening, to allow the lid envelope to be evacuated and the vacuum in the envelope to be checked and restored if necessary.

It will thus be seen that the walls of the container 10 prevent heat transfer by all three of the normal mechanisms (conduction, convection and radiation). Heat conduction through the wall is prevented by the low thermal conductivity of the expanded silica material forming the middle layer 30. Convection cannot take place as the envelope is evacuated, and so there is no fluid through which convection can occur. Heat transfer through radiation is prevented by the metallized layer(s) of the inner and/or outer wall 40, 20, which attenuates any incident radiation, and the presence of the materials in the expanded silica material of the middle layer 30, which reflect, absorb and/or scatter any infra-red radiation which has passed through the outer wall 20.

Figures 3, 5:
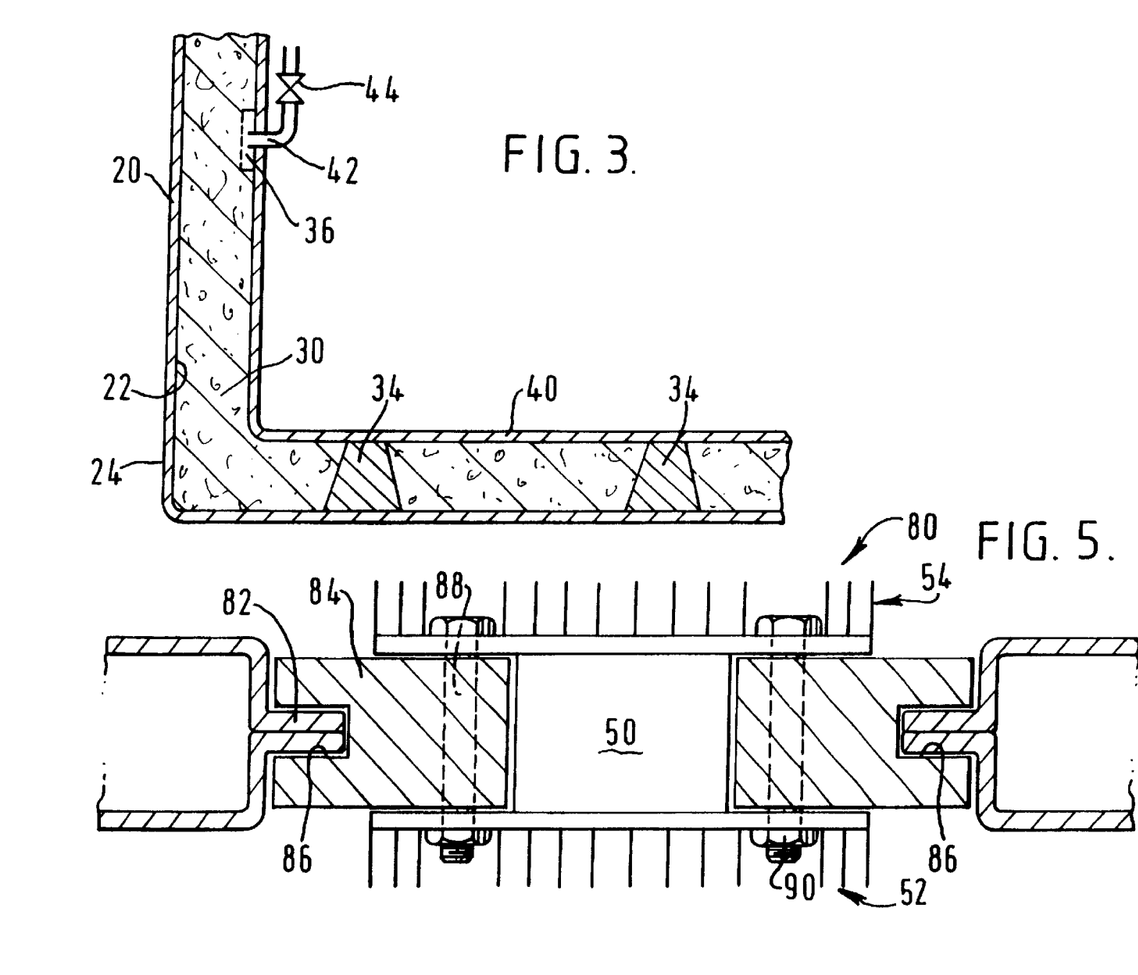
FIG. 3 is a fragmentary schematic cross-sectional view showing a variant construction of a wall of the first embodiment of the container.
FIG. 5 is a fragmentary cross-sectional view of the lid of a third embodiment of the container.

In an alternative construction shown in FIG. 3, the rigid expanded silica material can be replaced by granules of expanded silica. However, it is then necessary for the outer wall 20 to be relatively strong, and it may also be necessary to provide spacers 34 between the outer and inner layers to maintain a spacing between them. In addition, means must be provided to ensure that the granules are not sucked out by the vacuum pump when the space between the inner and outer walls is evacuated. This means can take the form of a screen 36 across the end of the passageway 42.

The container described above is intended to keep its contents at a certain temperature irrespective of ambient temperature, and may be a portable container, e.g. a food or medical container. It will be appreciated however that the wall construction is also applicable to other types of container, such as refrigerators, freezers or refrigerated vehicles.

If the container is to be used as a portable food or medical container, then it is necessary that the temperature of the contents stays within certain bounds. Medical materials in particular, such as organs for transplant and certain temperature-sensitive drugs, are easily damaged by being kept at inappropriate temperatures.

Figure 4:
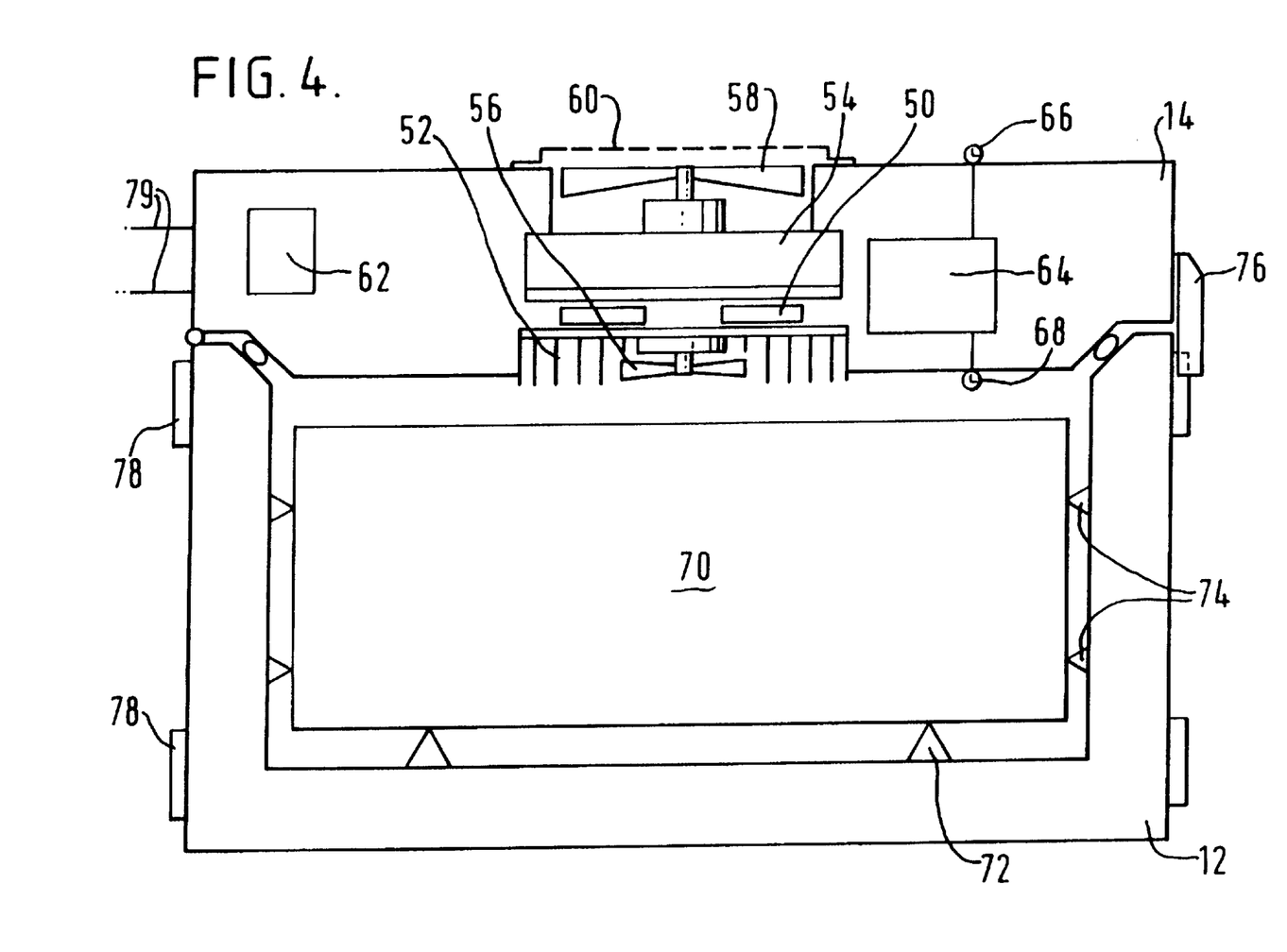
FIG. 4 is a cross-sectional view through a second embodiment of the container.

In a second preferred embodiment of the invention, as shown in FIG. 4 in particular, the container is provided with a thermoelectric module 50 which exploits the Peltier effect, for heating and/or cooling the contents of the container.

When a direct current passes around a circuit incorporating two different metals, one of the junctions between the two metals is heated and the other cooled. Which junction is heated and which is cooled depends on the direction of the current. A similar effect arises if certain semiconductors are used instead of metals. This generation and absorption of heat can be used to provide a heat pump, and the direction in which heat is pumped depends on the direction of current flow. Heat pumps using the Peltier effect are well known, and will not be described further here.

In the embodiment shown in FIG. 4, a Peltier effect thermoelectric module 50 is mounted in the lid of the container. The module itself is connected between an inner heat sink 52 and an outer heat sink 54, both of which are formed from aluminium, which provides a good balance between thermal efficiency and light weight. The heat sinks are provided with fins to provide an increased surface area for heat transfer. Each heat sink is in intimate thermal contact with a face of the Peltier effect module 50.

Both heat sinks are provided with electrically powered fans 56, 58 associated therewith. The fan 56 associated with the inner heat sink 52 is arranged to drive air from the inside of the container against the inner heat sink 52. Heat energy in the air is then transferred to the heat sink by forced convection, and the air is thus cooled. The fan 58 associated with the outer heat sink 54 is arranged to draw atmospheric air through ducts in the lid 14 (not shown) and through the channels between the fins. The air is then heated by the heat sink 54 and exhausted through a grille 60 in the top of the lid, to transfer heat from the outer heat sink 54 to the environment.

The Peltier effect module 50 and the heat sinks 52, 54 can be used to heat or cool the interior of the container 10. When the interior of the container needs to be cooled, electricity is supplied to the Peltier effect module 50 so as to pump heat from the inner heat sink 52 to the outer one 54. As a result, the inner heat sink is cooled, and the outer heat sink is heated. The fan 56 associated with the inner heat sink 52 is driven to bring air within the container against the inner heat sink 52, and this air is cooled as a result. Meanwhile, the fan 58 associated with the outer heat sink 58 is activated to draw air past the outer heat sink 58 and discharge it into the atmosphere. This air is heated as it goes past the outer heat sink 54, and thus draws heat from the outer heat sink. The net effect is to discharge heat from the interior of the container to the outside.

When it is necessary to heat the contents of the container, the direction of current supply to the Peltier device 50 is reversed, so that heat is pumped from the outer heat sink 54 to the inner one 52. The outer heat sink 54 is cooled as a result, while the inner heat sink 52 is heated. The fan 56 associated with the inner heat sink 52 drives air in the container against the inner heat sink 52 to heat the air, and thus heat the interior of the container. The air which is in contact with the outer heat sink 54 will serve to heat it, and as a result the air outside will be cooled. There is generally no need to activate the fan 58 associated with the outer heat sink. Thus the net effect of operating the module in this way is to draw heat from outside of the container into its interior.

The Peltier effect module 50 allows the temperature of the interior of the container to be varied within a range of around 60° C., allowing the temperature of the contents to differ by up to 30° C. from the external temperature. For example, in tropical areas, the contents of the container could be stored at 10° C. even if the outside temperature were 40° C., and the contents of the container can be prevented from freezing even if the external temperature approaches −30° C.

The decision as to whether to heat or cool the interior of the container is made by a control unit 62, which is programmed with the desired temperature for the interior of the container. The control unit receives signals from a thermostat unit 64, which is in turn connected to temperature sensors 66, 68, located on both the upper and lower surfaces of the lid, and also on the lower floor of the container (not shown). The control unit 62 compares the signals from the thermostat unit 64 with the desired temperature, and decides whether to operate the Peltier effect module 50 to heat or cool the interior of the container.

As can be seen from FIG. 4, the container includes a removable inner receptacle 70, and it is this inner container which actually holds the materials (drugs, organs or the like) which are transported in the container 10. Use of such an inner receptacle 70 confers a number of advantages. For example, the inner receptacle 70 can be made so as to be autoclavable. It is then possible to carry infectious or contaminated materials in the inner receptacle, and sterilize it by autoclaving. There is no need to sterilize the main container 10, as it has not come into contact with the infectious or contaminated material. Further, the inner receptacle 70 can be loaded with drugs and refrigerated separately to cool it. When it is necessary to transport the drugs, the inner receptacle 70 can simply be placed into the main container 10 and maintained at a low temperature by the Peltier effect module 50. There is no need to use the Peltier effect module to carry out the initial cooling of the inner receptacle or its contents.

The walls and floor of the base 12 and the lid 14 of the container 10 form an outer housing and preferably have the type of thermal insulation described in relation to FIGS. 1 to 3.

The inner receptacle is supported in the outer container on posts 72, 74 projecting inwardly from the walls and floor of the base 12 of the container 10. Posts may also project downwardly from the inner surface of the lid 14, although these are not shown. The purpose of the posts is to ensure that air can circulate in the gap around the exterior of the inner receptacle 70. In addition, the posts projecting downwardly from the lid bear on the top of the inner receptacle 70, and ensure that it is properly located in the main container 10 and cannot open accidentally.

Further, the container 10 is provided with lashing points 78, which allow it to be secured to a vehicle.

It will be appreciated that the temperature inside the inner receptacle 70 should preferably be as spatially uniform as possible, in other words, "hot spots" are to be avoided.

In order to avoid such hot spots, the air inside the main container 10 is circulated around the inner receptacle 70, so that the whole of the outside of the inner receptacle is kept at a generally uniform temperature. This circulation is achieved in part by the fan 56 associated with the inner heat sink 52, and in part (when the interior of the container is being cooled) by colder air moving downwardly from the inner heat sink 52, displacing warmer air upwards. It is also possible for the inner receptacle 70 to be formed with openings, so that air can then be circulated through it; however, it is then not usually possible to carry infectious or contaminated material, as there is a risk that they will leak into the main container 10.

The temperature at which the contents of the container are to be maintained can be entered into the control unit 62 in any suitable manner, and a number of alternatives are given in the introduction. In addition the control unit can include a temperature logging system, and can generate alarm signals if the set temperature is exceeded or if the latches holding the container closed are opened, as described above.

As the container is intended to be portable, the power for the Peltier device 50, the control unit 62 and the fan motors is derived from a battery (not shown). The battery is rechargeable, and can be recharged through power leads 79. For convenience, the battery is provided in the lid of the container. A back-up power source is also provided, in the form of a second battery (not shown), so that even if the main battery is exhausted the container can still regulate the temperature of its contents. The control unit generates an alarm signal on failure or exhaustion of the main battery, and a further different alarm signal when the back-up battery falls below a predetermined proportion of its capacity.

As will be appreciated, the medical container has a number of applications. Its robustness and ability to function in a wide range of temperature conditions allows it to be used in areas where more delicate refrigerated containers are not suitable.

However, Peltier effect modules are generally relatively fragile, and should not be exposed to high decelerations. High decelerations can result when the container is dropped, subjected to impacts or the like. It is thus necessary to ensure that the Peltier effect module 50 in the container is not exposed to high decelerations when the container as a whole is.

Figure 6:
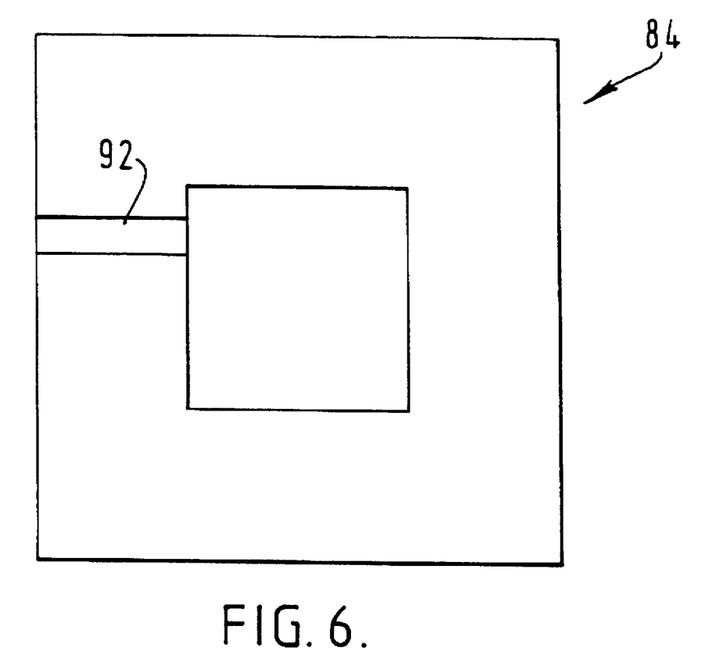
FIG. 6 is a plan view of a part of the lid of the third embodiment of the container.
Figure 7:
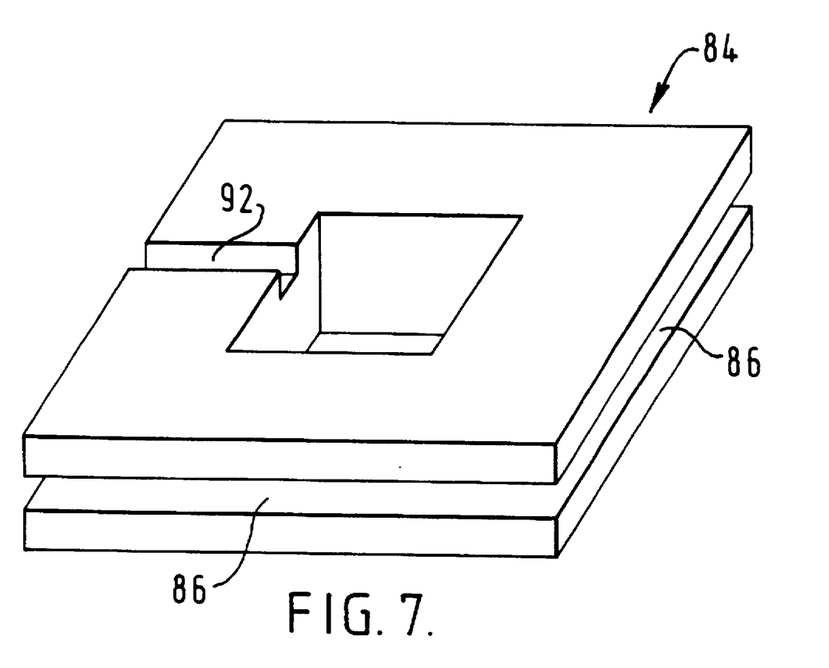
FIG. 7 is a perspective view of the same part of the lid of the third embodiment of the container.

This is achieved in the embodiment shown in FIGS. 5 to 7 by placing the Peltier effect module 50 in a flexible structure 80, which absorbs the deceleration and protects the module from damage. A cross-section of a part of the lid 14 of the container is shown in FIG. 5. Most of the lid is formed from panels employing vacuum technology, as previously described. However, a hole is formed in the centre of the lid, and the edges of the hole are formed from the inner and outer walls of the vacuum panels, which are formed into projecting tongues 82 as shown.

A frame-shaped elastomeric member 84 is positioned in the hole, and the member is best shown in FIGS. 6 and 7. As will be seen, the edges of the frame are formed with grooves 86, and these grooves accommodate the tongues 82 of the vacuum panels to locate the member in place. The centre of the frame-shaped member 84 is sized to accommodate the Peltier effect module 50.

The inner and outer heat sinks 52, 54 are attached to the top and bottom of the Peltier effect module 50, and are located in place relative to the frame-shaped member by nylon bolts 88, which pass through both of the heat sink members 52, 54 and the frame-shaped member 84. The bolts are secured in place by nylon nuts 90. Nylon nuts and bolts are used to prevent there being a direct path of good heat conduction between the inner and outer heat sinks, which would arise if metallic bolts were to be used.

As shown in FIGS. 6 and 7, a channel 92 is formed in the upper surface of the frame-shaped member 84 to accommodate the power leads linking the Peltier effect module and the fan motors to the power supply.

The elastomeric member will absorb shock loads applied to the container as a whole, and reduces the deceleration experienced by the Peltier effect module. Containers with the Peltier effect module mounted in such a member have greatly improved resistance to shock and impacts.

What is claimed is:

1. A portable container for receiving contents for transport while regulating the temperature of the contents, the portable container comprising heating and/or cooling means in the form of a Peltier effect device, a removable inner receptacle for receiving the contents, and a control unit for controlling the Peltier effect device;

characterized in that the inner receptacle occupies most of the space in the container, with an air gap around substantially the entire periphery of the removable inner receptacle, and in that the control unit controls the Peltier effect device so as to regulate the temperature of the air around the outside of the inner receptacle and thereby regulate the temperature of the contents of the inner receptacle.

2. A container as claimed in claim 1, comprising projections which extend from an outer housing of the container to support the inner container.

3. A container as claimed in claim 1, wherein said control unit is arranged to store a desired temperature for the contents of the container, to receive a signal from a temperature sensor located within the container, and to generate a signal to control the Peltier effect device.

4. A container as claimed in claim 3, wherein a keypad is mounted on the container for entering the desired temperature.

5. A container as claimed in claim 3, wherein the container comprises an electromagnetic or ultrasonic receiver, and the desired temperature is set using an external transmitter.

6. A container as claimed in claim 3, wherein the container is connectible to a computer for setting the desired temperature.

7. A container as claimed in claim 3, wherein said control unit generates an alarm signal if the temperature in the container strays too far from the desired temperature.

8. A container as claimed in claim 1, wherein said control unit comprises a temperature logging system, said temperature logging system providing means to verify the temperature history of the container.

9. A container as claimed in claim 8, wherein said temperature logging system is arranged to sample the temperature at intervals, and to print the sampled temperatures.

10. A container as claimed in claim 9, wherein a backup power source is provided.

11. A container as claimed in claim 10, wherein the Peltier device is connected to an inner heat sink facing the interior of the container and an outer heat sink facing the exterior of the container, the heat sinks being clamped together by clamping means passing through the heat sinks and the elastomeric member.

12. A container as claimed in claim 11, wherein the clamping means are nylon bolts.

13. A container as claimed in claim 12, wherein the insulating material is rigid.

14. A container as claimed in claim 13, wherein the inner surface of the outer wall is metallized.

15. A container as claimed in claim 12, wherein the insulating material hinders the passage of infra-red radiation.

16. A container as claimed in claim 12, wherein the outer wall is metallized.

17. A container as claimed in claims 12, wherein the outer wall includes a metallic foil layer.

18. A container as claimed in claim 12, wherein the inner wall is metallised.

19. A container as claimed in claim 12, wherein the inner wall includes a metallic foil layer.

20. A container as claimed in claim 19, wherein the passageway is provided with a valve, the valve normally being closed.

21. A container as claimed in claim 12, comprising a passageway to allow the space between the inner and outer walls to be communicated with a region outside of the space.

22. A container as claimed in claim 21 or 20, wherein the inner wall is provided with the passageway.

23. A container as claimed in claim 1, wherein the power for the heating and/or cooling means and the control unit is derived from a battery.

24. A container as claimed in claim 1, wherein the heating and/or cooling means is mounted in a block of elastomeric material.

25. A container as claimed in claim 1, comprising an outer housing in the form of an inner wall and an outer wall defining a space therebetween, wherein the space between the inner and outer walls is at least partially evacuated and is occupied by a solid thermally insulating material.

26. A container as claimed in claim 25, wherein the metallisation or the metallic foil layer is provided with means for making an electrical connection to provide an electrostatic shield.

27. A portable container having heating and/or cooling means in the form of a Peltier effect device, wherein the Peltier device is mounted in a block of elastomeric material which is in turn mounted to a housing of the container.

28. A container as claimed in claim 27, wherein the clamping means is formed from an insulating material.

* * * * *